United States Patent
Naya

[11] Patent Number: 5,875,032
[45] Date of Patent: Feb. 23, 1999

[54] SURFACE PLASMON SENSOR HAVING AN IMPROVED OPTICAL SYSTEM

[75] Inventor: Masayuki Naya, Kanagawa-ken, Japan

[73] Assignee: Fuji Photo Film Co., Ltd., Kanagawa, Japan

[21] Appl. No.: 840,648

[22] Filed: Apr. 25, 1997

[30] Foreign Application Priority Data

Apr. 30, 1996 [JP] Japan .................................. 8-109366

[51] Int. Cl.$^6$ .................................................. G01N 21/55
[52] U.S. Cl. ........................................... 356/445; 356/446
[58] Field of Search ..................................... 356/445–446

[56] References Cited

U.S. PATENT DOCUMENTS

| | | | |
|---|---|---|---|
| 4,844,613 | 7/1989 | Batchelder et al. | 356/445 |
| 4,889,427 | 12/1989 | Van Veen et al. | 356/445 |
| 4,997,278 | 3/1991 | Finlan et al. | 356/445 |
| 5,047,213 | 9/1991 | Finlan et al. | 356/445 |
| 5,313,264 | 5/1994 | Ivarsson et al. | 356/445 |
| 5,341,215 | 8/1994 | Seher | 356/445 |
| 5,485,277 | 1/1996 | Foster et al. | 356/445 |
| 5,629,213 | 5/1997 | Kornguth et al. | 356/445 |

FOREIGN PATENT DOCUMENTS 6-167443  6/1994  Japan .

*Primary Examiner*—Robert Kim
*Attorney, Agent, or Firm*—Sughrue, Mion, Zinn, Macpeak & Seas, PLLC

[57] ABSTRACT

A surface plasmon sensor includes a prism, a metal film which is formed on one face of the prism and is brought into contact with a sample, a light source emitting a light beam, and an optical system which causes the light beam to enter the prism so that various angles of incidence of the light beam to the interface between the prism and the metal film can be obtained. First and second photodetectors respectively detect the amounts of light of first and second parts of the light beam reflected in total reflection from the interface. The first part is a light bundle reflected from the interface at angles in a first reflecting angle range and the second part is a light bundle reflected from the interface at angles in a second reflecting angle range different from the first reflecting angle range. A comparator compares the light amount signal output from the first photodetector with that output from the second photodetector.

6 Claims, 2 Drawing Sheets

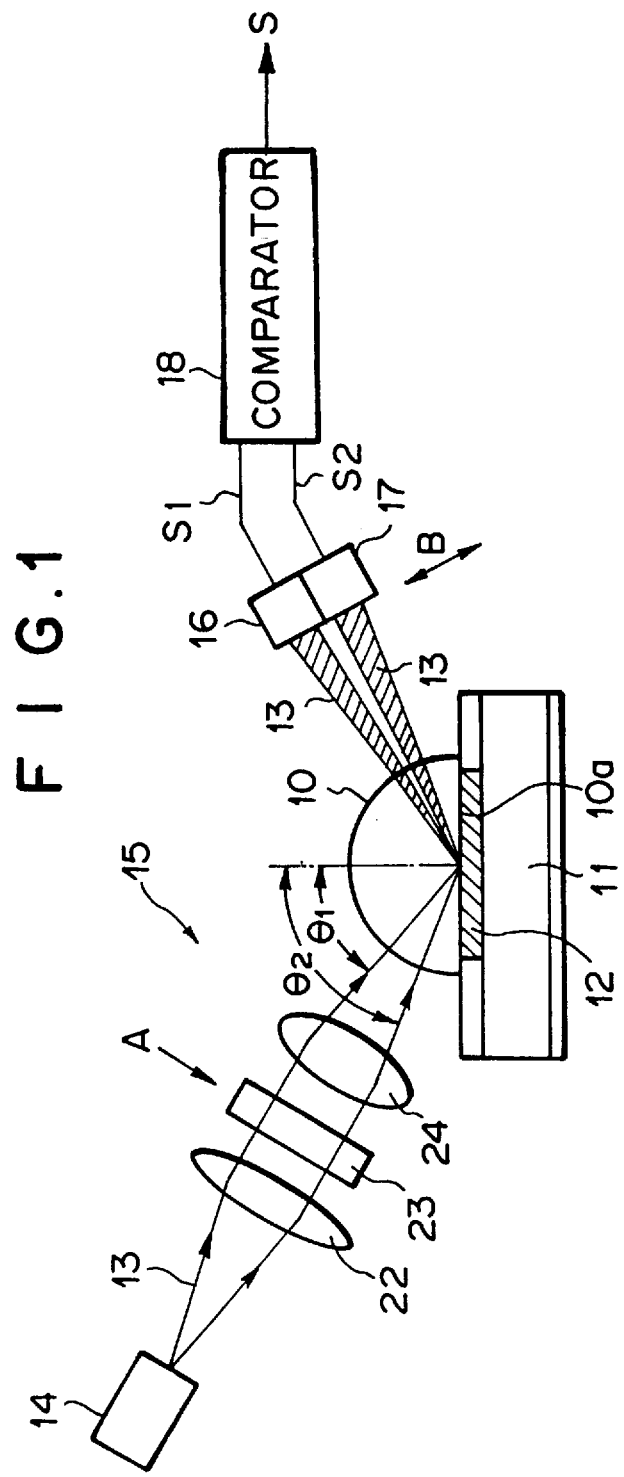

SURFACE PLASMON SENSOR HAVING AN IMPROVED OPTICAL SYSTEM

BACKGROUND OF THE INVENTION

1. Field of the Invention

This invention relates to a surface plasmon sensor for quantitatively analyzing a material in a sample utilizing generation of surface plasmon, and more particularly to a surface plasmon sensor in which the light detecting system is simplified in structure.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon sensor using the Kretschmann configuration basically comprises a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, and a photodetector means which is able to detect the intensity of the light beam reflected in total reflection from the interface for the various angles of incidence.

In order to obtain various angles of incidence of the light beam to the interface, a relatively thin incident light beam may be caused to impinge upon the interface while deflecting the incident light beam or a relatively thick incident light beam may be caused to converge on the interface so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, components of light reflected from the interface at various angles may be detected by an area sensor.

In such a plasmon sensor, when a light beam impinges upon the metal film at a particular angle of incidence θsp which is at least as great as the angle of total internal reflection, evanescent waves having an electric field distribution are generated in the sample in contact with the metal film and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total reflection from the interface between the prism and the metal film sharply drops.

When the wave number of the surface plasmon can be known from the angle of incidence θsp at which the phenomenon takes place, the dielectric constant of the sample can be obtained. That is, $$Ksp(\overline{\omega}) = \frac{\overline{\omega}}{c} \sqrt{\frac{\epsilon_m(\overline{\omega})\epsilon_s}{\epsilon_m(\overline{\omega}) + \epsilon_s}}$$

wherein Ksp represents the wave number of the surface plasmon, ω represents the angular frequency of the surface plasmon, c represents the speed of light in a vacuum, and εm and εs respectively represent the dielectric constants of the metal and the sample.

When the dielectric constant εs of the sample is known, the concentration of a specific material in the sample can be determined on the basis of a predetermined calibration curve. Accordingly, a specific component in the sample can be quantitatively analyzed by detecting the angle of incidence θsp at which the intensity of light reflected in total reflection from the interface between the prism and the metal film sharply drops.

In such a surface plasmon sensor, there has been a problem that since a photodetector which is moved in synchronization with deflection of the incident light beam or a CCD area sensor having a wide light receiving surface is required in order to detect the intensity of the light beam reflected from the interface between the prism and the metal film, the cost of the system is high.

SUMMARY OF THE INVENTION

In view of the foregoing observations and description, the primary object of the present invention is to provide a surface plasmon sensor which is simple in structure of the light detecting system and accordingly can be produced at relatively low cost.

In accordance with the present invention, there is provided a surface plasmon sensor comprising a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, first and second photodetectors which respectively detect the amounts of light of first and second parts of the light beam reflected in total reflection from the interface, the first part being a light bundle reflected from the interface at angles in a first reflecting angle range and the second part being a light bundle reflected from the interface at angles in a second reflecting angle range different from the first reflecting angle range, and a comparator which compares the light amount signal output from the first photodetector with that output from the second photodetector.

As the first and second photodetectors, for instance, a two-segment photodiode can be used.

When a light beam impinges upon the interface between the prism and the metal film and is reflected in total reflection from the interface, the relation between the angle of incidence θ of the light beam to the interface and the intensity I of the reflected light is substantially as shown by curve a in FIG. 2A or curve b in FIG. 2B. θsp in FIGS. 2A and 2B is the angle of incidence at which the intensity of light reflected in total reflection from the interface between the prism and the metal film sharply drops due to excitation of surface plasmon.

Assuming that the first reflecting angle range is continuous with the second reflecting angle range and the boundary therebetween is θM, the amount of light of a light bundle impinging upon the interface at angles smaller than θM is detected by one of the first and second photodetectors and that of a light bundle impinging upon the interface at angles larger than θM is detected by the other photodetector.

Assuming that the amount of light of the light bundle impinging upon the interface at angles smaller than θM is detected by the first photodetector and that of the light bundle impinging upon the interface at angles larger than θM is detected by the second photodetector, the first photodetector detects a light bundle in the hatched range in FIG. 2A or FIG. 2B. The amount of light detected by the first photodetector is larger in the case shown in FIG. 2B than in the case shown in FIG. 2A. On the other hand, the amount of light detected by the second photodetector is smaller in the case shown in FIG. 2B than in the case shown in FIG. 2A. Thus there is a specific difference between the amount of light detected by the first photodetector and that detected by the second photodetector according to the relation between the angle of incidence θ and the intensity I of the reflected light.

Accordingly, when referring to a calibration curve or the like for each sample which is obtained in advance, said particular angle of incidence θsp and the relation between the angle of incidence θ and the intensity I of the reflected light can be estimated on the basis of a differential signal or the like obtained by passing the light amount signals from the first and second photodetectors through the comparator, whereby a specific material in the sample can be quantitatively analyzed.

Even if the first and second reflecting angle ranges are not continuous with each other, there is a specific difference between the amount of light detected by the first photodetector and that detected by the second photodetector according to the relation between the angle of incidence θ and the intensity I of the reflected light and accordingly analysis of a material in the sample can be effected in the same manner.

As can be understood from the description above, since the light detecting system of the surface plasmon sensor in accordance with the present invention is formed of a pair of photodetectors which may comprise, for instance, a two-segment photodiode which is simple in structure, and at the same time, the comparator associated with the first and second photodetectors is also simple in structure, the surface plasmon sensor of the present invention can be produced at very low cost as compared with the conventional surface plasmon sensors where a movable photodetector, a CCD area sensor having a wide light receiving surface or the like is used.

BRIEF DESCRIPTION OF THE DRAWINGS

FIG. 1 is a side view of a surface plasmon sensor in accordance with an embodiment of the present invention.

DESCRIPTION OF THE PREFERRED EMBODIMENT

Figure 2A:
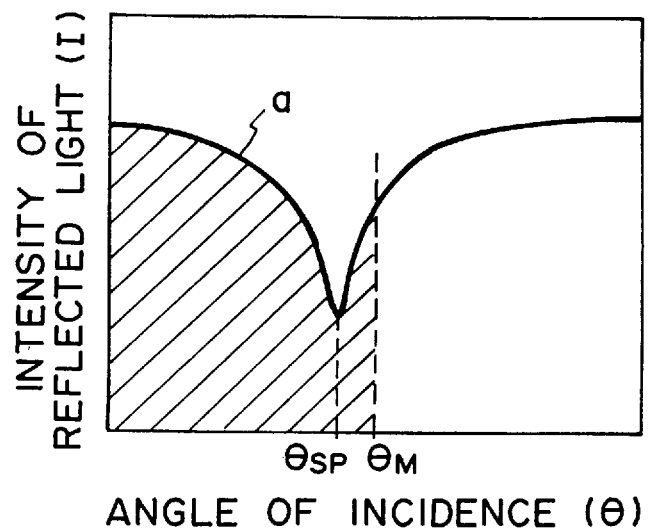
FIGS. 2A and 2B are graphs showing the relation between the angle of incidence of a light beam and the output of the photodetectors in a surface plasmon sensor.

In FIG. 1, a surface plasmon sensor in accordance with an embodiment of the present invention comprises a semicylindrical prism 10, a metal film 12 such as of gold, silver or the like which is formed on one face (the lower face as seen in FIG. 1) of the prism 10 and brought into contact with a sample 11, a light source 14 such as a semiconductor laser emitting a single light beam 13, an optical system 15 which causes the light beam 13 to enter the prism 10 so that various angles of incidence of the light beam 13 to the interface 10a between the prism 10 and the metal film pieces 12 can be obtained, first and second photodetectors 16 and 17 which detects the amount of light of the light beam 13 reflected in total reflection from the interface 10a and a comparator 18 connected to the first and second photodetectors 16 and 17.

The optical system 15 comprises a pair of cylindrical lenses 22 and 24 which converge the diverging light beam 13 emitted from the light source 14 only in a plane normal to the longitudinal axis of the prism 10 and another cylindrical lens 23 which collimates the light beam 13 as seen in the direction of arrow A in FIG. 1.

Since the light beam 13 is converged on the interface 10a by the cylindrical lenses 22 and 24, the light beam 13 impinging upon the interface 10a contains components which impinge upon the interface 10a at various angles θ. In FIG. 1, θ1 denotes a minimum angle of incidence and θ2 denotes a maximum angle of incidence. The angle of incidence θ being at least as great as an angle of total inner reflection. The light beam 13 is reflected in total reflection from the interface 10a and accordingly the reflected light beam 13 contains components which are reflected from the interface 10a at various angles.

The first and second photodetectors 16 and 17 may comprise, for instance, a two-segment photodiode. The first photodetector 16 detects the amount of light of the components of the light beam 13 reflected from the interface 10a at angles in a first reflecting angle range (relatively small angle range) and the second photodetector 17 detects the amount of light of the components of the light beam 13 reflected from the interface 10a at angles in a second reflecting angle range (relatively large angle range). The first and second reflecting angle ranges are hatched portions in FIG. 1.

Analysis of a sample by the surface plasmon sensor of this embodiment will be described, hereinbelow.

That is, the sample 11 is placed in contact with the metal film 12. When effecting analysis, a light beam 13 is emitted from the light source 14 and the light beam 13 is converged on the metal film 12 through the cylindrical lenses 22 and 24. The light beam 13 reflected in total reflection from the interface 10a between the metal film 12 and the prism 10 is detected by the first and second photodetectors 16 and 17.

Light amount signals S1 and S2 respectively output from the first and second photodetectors 16 and 17 are input into the comparator 18 and the comparator 18 outputs a differential signal S representing the difference between the light amount signals S1 and S2.

Figure 2B:
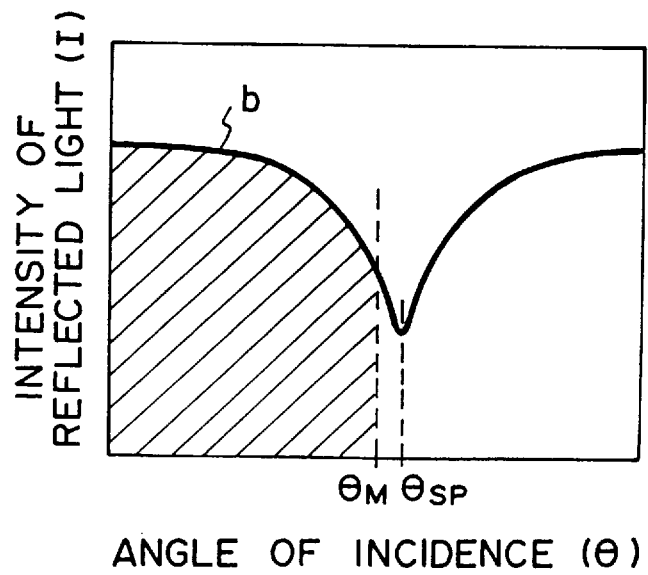

As described in detail before, a light beam impinging upon the interface 10a at a particular angle of incidence θsp excites surface plasmon in the interface 10a, and the intensity I of the light reflected from the interface 10a at an angle corresponding to the angle θsp greatly drops. That is, the relation between the angle of incidence θ of the light beam to the interface 10a and the intensity I of the reflected light is substantially as shown by curve a in FIG. 2A or curve b in FIG. 2B. When the value of the particular angle of incidence θsp and the relation between the angle of incidence θ of the light beam to the interface 10a and the intensity I of the reflected light are known, a specific material in the sample 11 can be quantitatively analyzed.

In the conventional surface plasmon sensors, the value of the particular angle of incidence θsp and the relation between the angle of incidence θ of the light beam to the interface 10a and the intensity I of the reflected light are obtained by detecting the intensity distribution of the reflected light in the direction of arrow B in FIG. 1. In this embodiment, these value and relation are obtained on the basis of the differential signal S output from the comparator 18.

As can be understood from the description above, since the light detecting system of the surface plasmon sensor of this embodiment is formed of the first and second photodetectors 16 and 17 which may comprise, for instance, a two-segment photodiode which is simple in structure, and at the same time, the comparator 18 associated with the first and second photodetectors 16 and 17 is also simple in structure, the surface plasmon sensor of this embodiment can be produced at very low cost.

What is claimed is:

1. A surface plasmon sensor comprising a prism, a metal film which is formed on one face of the prism and is brought into contact with a sample, a light source emitting a light beam, an optical system which causes the light beam to enter the prism so that various angles of incidence of the light beam to the interface between the prism and the metal film can be obtained, first and second photodetectors which respectively detect the amounts of light of first and second parts of the light beam reflected in total reflection from the interface, the first part being a light bundle reflected from the interface at angles in a first reflecting angle range and the second part being a light bundle reflected from the interface at angles in a second reflecting angle range different from the first reflecting angle range, and a comparator which compares the light amount signal output from the first photodetector with that output from the second photodetector.

2. A surface plasmon sensor comprising:

a prism having a longitudinal axis;

a metal film formed on a face of the prism to define an interface therebetween, the metal film for contacting a sample;

a light source for emitting a light beam;

an optical system for receiving the light beam and converging the light beam in a plane normal to the longitudinal axis of the prism, such that the light beam enters the prism and impinges the interface simultaneously at incident angles within an incident angle range;

a first and a second photodetector for respectively detecting an amount of light of a first and a second part of the light beam reflected from the interface, the first part being reflected from the interface at angles in a first reflecting angle range and the second part being reflected from the interface at angles in a second reflecting angle range, the first and the second photodetectors generating respective output signals based on the amount of light detected; and a comparator coupled to the first and the second photodetectors for receiving and comparing the output signal from the first photodetector to the output signal from the second photodetector.

3. A surface plasmon sensor according to claim 1, wherein the light source emits a divergent light beam, and the optical system further comprises:

a pair of cylindrical lenses arranged in series, said pair of cylindrical lenses for converging the divergent light beam; and an collimating lens positioned between the pair of cylindrical lenses.

4. A surface plasmon sensor according to claim 1, wherein the first and the second angle ranges are not continuous with each other.

5. A surface plasmon sensor according to claim 1, wherein the first and the second angle ranges are continuous with each other.

6. A surface plasmon sensor according to claim 1, wherein the incident angles within the incident angle range are at least as great as an angle of total inner reflection.

* * * * *